United States Patent [19]

Hanifin, Jr. et al.

[11] 4,044,021

[45] Aug. 23, 1977

[54] TETRASUBSTITUTED IMIDAZOLIDINE DIURETICS USEFUL IN THE TREATMENT OF HYPERALDOSTERONISM

[75] Inventors: John William Hanifin, Jr.; Robert Zalmon Gussin, both of Suffern; Elliott Cohen, Pearl River, all of N.Y.

[73] Assignee: American Cyanamid Company, Stamford, Conn.

[21] Appl. No.: 293,874

[22] Filed: Oct. 2, 1972

Related U.S. Application Data

[63] Continuation-in-part of Ser. No. 191,470, Oct. 21, 1971, abandoned.

[51] Int. Cl.$^2$ .......................................... C07D 233/88
[52] U.S. Cl. .................. 548/312; 260/307 F; 260/309.6; 260/455 R; 260/465 D; 260/471 A; 260/518 R; 260/558 A; 424/273 R; 548/314

[58] Field of Search ...................................... 260/309.7

[56] References Cited

U.S. PATENT DOCUMENTS 2,557,911  6/1951  Hoegberg ........................ 260/309.7

FOREIGN PATENT DOCUMENTS 2,002,196  2/1969  France ............................ 260/309.7

OTHER PUBLICATIONS

Ugi et al. Chem. Ber., vol. 97, pp. 2276-2281 (1964).

Primary Examiner—Natalie Trousof
Attorney, Agent, or Firm—Charles F. Costello, Jr.

[57] ABSTRACT 1-(phenyl or p-chlorophenyl)-2,4(imino, methylimino or oxo)-disubstituted-3-methylimidazolidines and a method for inducing diuresis and treating hyperaldosteronism by the administration thereof.

6 Claims, No Drawings

TETRASUBSTITUTED IMIDAZOLIDINE DIURETICS USEFUL IN THE TREATMENT OF HYPERALDOSTERONISM

CROSS REFERENCE TO RELATED APPLICATION

This application is a continuation-in-part of our copending application Ser. No. 191,470 filed Oct. 21, 1971, now abandoned.

BRIEF SUMMARY OF INVENTION

This invention relates to new and useful 1-(phenyl or p-chlorophenyl)-2,4-disubstituted-3-methylimidazolidines and to a method for treating hyperaldosteronism and inducing diuresis by the administration thereof. It has been found that certain tetrasubstituted imidazolidines and pharmaceutically acceptable salts thereof cause diuresis without the loss of significant amounts of potassium and thus find considerable utility in the treatment of edema and hypertension. It has also been found that they demonstrate antialdosteronic activity in mammals.

Aldosterone is a naturally occurring, potent mineralocorticoid which is involved in various physiologic processes involved in sodium, potassium and water homeostasis. An excess of this material results in a condition termed hyperaldosteronism which is present in a number of pathological conditions, such as cirrhosis with ascites, nephrosis, cardiac failure, idiopathic edema, adrenocortical tumor, adrenocortical hyperplasia, renal artery stenosis and malignant hypertension. Fluid and electrolyte imbalance often occurs in the preceding conditions due to the hyperaldosteronism. This imbalance can be corrected by agents which produce natriuresis without kaliuresis. The diuretic effect of the tetrasubstituted imidazolidines of this invention is primarily due to the antagonism of aldosterone but in part results from an additional direct renal tubular effect.

The novel 1-(phenyl or p-chlorophenyl)-2,4-disubstituted-3-methyl-imidazolidines of this invention may be represented by the formula:

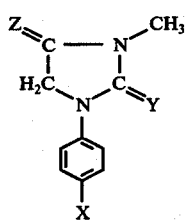

wherein X is selected from the group consisting of hydrogen and chlorine; Y and Z are each selected from the group consisting of NH, NCH₃ and O, with the proviso that both Y and Z are not O in the same compound; and the pharmaceutically acceptable salts thereof. In addition, useful compositions of matter are disclosed utilizing the above said compounds, alone or in combination with other useful therapeutic agents.

Representative groups of tetrasubstituted imidazolidines encompassed by this invention are the 1-(phenyl or p-chlorophenyl)-2-imino-3-methyl-4-oxoimidazolidines, 1-(phenyl or p-chlorophenyl)-2-methylimino-3-methyl-4-oxoimidazolidines, 1-(phenyl or p-chlorophenyl)-2-imino-3-methyl-4-methyliminoimidazolidine, 1-(phenyl or p-chlorophenyl)-4-imino-3-methyl-2-oxoimidazolidines, 1-(phenyl or p-chlorophenyl)-3-methyl-4-methylimino-2-oxoimidazolidines and the like. The most preferred compounds of this invention are the tetrasubstituted imidazolidines, 1-phenyl-2-imino-3-methyl-4-oxoimidazolidine and 1-p-chlorophenyl-2-imino-3-methyl-4-oxoimidazolidine, and their hydrochloride salts. These tetrasubstituted imidazolidines have exhibited the most outstanding diuretic and antialdosterone activity of the compounds tested.

BACKGROUND OF THE INVENTION

Our application Ser. No. 191,470, now abandoned, was broadly concerned with inducing diuresis and treating hyperaldosteronism by the administration of certain substituted phenyl-2-imino-2-imidazolin-4-ones and substituted phenyl-2-imino-3-substituted-4-imidazolidinones. The latter compounds can also be named as imidazolidines. It has now been found that some of the imidazolidines disclosed in our previous application possess undesirable properties which render them unsuitable for the intended purpose of this invention and such compounds have been excluded herefrom. Such compounds have been excluded on the basis of toxicity, such as death of the animals, crystallization in the urine, lesions in the kidney, great variability in diuretic activity and in effect on Na/K ratio, and failure to obtain an increase in diuretic activity and in Na/K ratio with increased dosage. For example, it has been found that the compound 1-(p-chlorophenyl)-2-amino-4-oxo-2-imidazoline, although active, is too toxic for use in that it causes crystalluria, as a result of its insolubility, and renal tissue damage in test animals. The compound 1-(3,4-dichlorophenyl)-2-amino-4-oxo-2-imidazoline has also been shown to be too toxic for use, in that it is lethal to animals, is toxic to blood cells, and causes crystalluria as well as congestion in the medulla of the kidney. The compounds 1-phenyl-2-imino-3-ethyl-4-oxoimidazolidine, 1-(p-chlorophenyl)-3-ethyl-2-imino-4-oxoimidazolidine and 1-(3,4-dichlorophenyl)-3-ethyl-2-imino-4-oximidazolidine, all disclosed in our application Ser. No. 191,470, although active, exhibit one or more undesirable properties which render them unsuitable for the use intended herein.

It has been shown that isomers of the compounds of the present invention, wherein the methyl group is merely moved from one nitrogen to another, are inactive for the purpose of this invention. Such inactive isomers are 1-phenyl-2-methylamino-4-oxo-2-imidazoline and 1-p-chlorophenyl-2-methylamino-4-oxo-2-imidazoline. It has also been shown that compounds are inactive or otherwise unsuitable for the purposes of this invention when the substitutent on the 3-position of the imidazolidine ring is other than a methyl or ethyl group. For example, compounds such as 1-(p-chlorophenyl)-2-imino-3-n-propyl-4-oxoimidazolidine, 1-phenyl-2-imino-3-n-propyl-4-oximidazolidine, and 1-(p-chlorophenyl)-2-imino-3-n-butyl-4-oxoimidazolidine have been shown to be inactive.

It has now been found that only a limited number of tetrasubstituted imidazolidines and the pharmaceutically acceptable salts thereof demonstrate sufficient diuretic effect to antialdosteronic activity when administered to animals, and are sufficiently non-toxic and otherwise desirable to warrant consideration for the purpose of this invention.

Certain 1-phenyl-2-imino-3-alkyl-4-oxoimidazolidines are disclosed, as glycocyamidines, in U.S. Pat. No. 2,557,911 and J. Am. Chem. Soc. 73: 2942 (1951). U.S.

Pat. No. 2,557,911, at column 4, lines 9–14 discloses that such imidazolidines are useful only as chemotherapeutic agents, bactericides and catalysts. There is no disclosure in that patent of their utility as diuretic agents or their use in the treatment of hyperaldosteronism. This type of diuretic action could not have been part of the utility in the patent above since the mineralocorticoid hormone, aldosterone, was not discovered until 1953 and the ability to antagonize its action and thereby produce a diuretic effect was not discovered until 1955. Moreover, at the time of the patent, a chemotherapeutic agent meant that such agent had to do with the treatment of infectious disease. The closest specific compound to those of this invention disclosed in the above patent is the compound 1-phenyl-3-ethylglycocyamidine or, by our nomenclature, 1-phenyl-2-imino-3-ethyl-4-oxoimidazolidine. This imidazolidine is not encompassed within the present invention. Tests have shown that 1-phenyl-2-imino-3-ethyl-4-oxoimidazolidine as well as 1-(p-chlorophenyl)-2-imino-3-ethyl-4-oxoimidazolidine, although active for the purpose of this invention, do not give a useful increase in diuretic activity and are otherwise unsuitable for the purposes of this invention. Tests have also shown that the higher alkyl compounds disclosed in U.S. Pat. No. 2,557,911, such as the specifically disclosed 1-phenyl-3-n-octylglycocyamidine (or 2-imino-4-oxoimidazolidine) and the broadly disclosed 1-phenyl-2-imino-3-n-propyl-4-oxoimidazolidine, 1-(p-chlorophenyl)-2-imino-3-n-propyl-4-oxoimidazolidine, and 1-(p-chlorophenyl)-2-imino-3-n-butyl-4-oximidazolidine, are inactive and therefore unsuitable for the purposes of this invention. A nitro-substituted compound is disclosed in the above references but such compounds, including also 1-(p-nitrophenyl)-2-imino-3-methyl-4-oxoimidazolidine, are inactive for the purposes of this invention, as also are a variety of other substituted-phenyl compounds. The scope of U.S. Pat. No. 2,557,911 comprises six categories of compounds: (1) 1-alkylglycocyamidines; (2) 1-arylglycocyamidines; (3) 1,3-dialkylglycocyamidines; (4) 1,3-diarylglycocyamidines; (5) 1-alkyl-3-arylglycocyamidines; and (6) 1-aryl-3-alkylglycocyamidines. In addition to the categories shown above to be inactive, those of cateogry 1 such as the specifically disclosed 1-n-octylglycocyamidine and of category 4 such as the specifically disclosed 1,3-diphenylglycocyamidine and 1-phenyl-3-(p-nitrophenyl)-glycocyamidine are also inactive for the purposes of this invention. As mentioned above, two compounds of category 2 were active but too toxic for use; the rest of the compounds tested were inactive. Therefore, only compounds of category 6 are the subject of the present invention and, furthermore, only a very small part, namely two compounds, of those comprising category 6 are within the scope of the present invention.

DETAILED DESCRIPTION OF THE INVENTION

The 1-(phenyl or p-chlorophenyl)-2,4-disubstituted-3-methylimidazolidines of this invention may be prepared by the following reaction sequences:

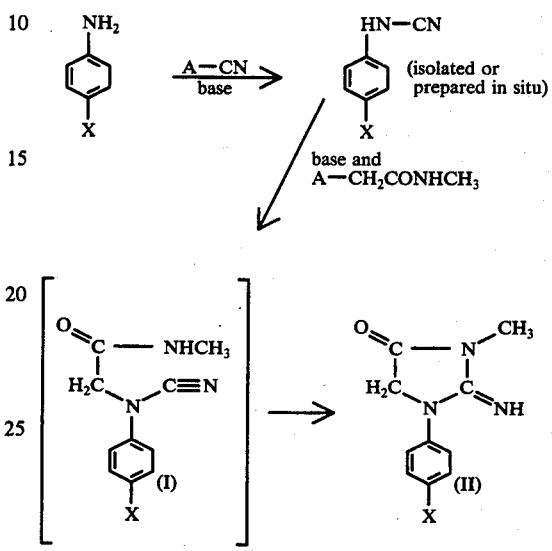

wherein X is as hereinbefore designated, A is defined as a leaving group such as halogen, cyano and trimethylammonium.

Generally the aniline or 4-chloroaniline compound is reacted with an agent such as cyanogen bromide in a basic solution, e.g., using excess substituted aniline compound, or other organic bases such as diisopropylethylamine, or inorganic bases such as KHCO₃, for 4–60 hours at 30°-80° C. Depending upon the reaction time, a temperature of from 20°-100° C. is deemed suitable. The substituted phenylcyanamide formed is dissolved in a strong base, such as aqueous sodium hydroxide or alcoholic sodium alkoxide and reacted with a compound such as a haloacetamide for 48 hours at room temperature for 4 hours at approximately 80° C. to yield the desired 1-(phenyl or p-chlorophenyl)-2,4-disubstituted-3-methylimidazolidine. Suitable solvents which may be used in both steps include alcohols, ketones, ethers, esters, nitriles, amides, sulfoxides, sulfones, hydrocarbons and others. The acyclic intermediate above (I) can be replaced with an isomeric intermediate (III) synthesized as below. In both instances, the intermediate need not be isolated. An alternative ring closure to that of III producing II is the cyclization of IV to II. The reaction sequence is the same except that H-Z' has been added to the cyano group throughout and it is then lost in the last step leading to II. The sequence proceeds through the chloroacetyl derivatives of methylguanidine, N,O-dimethylisourea, or N,S-di-methylisothiourea which are then aminated with aniline or p-chloroaniline, followed by cyclization.

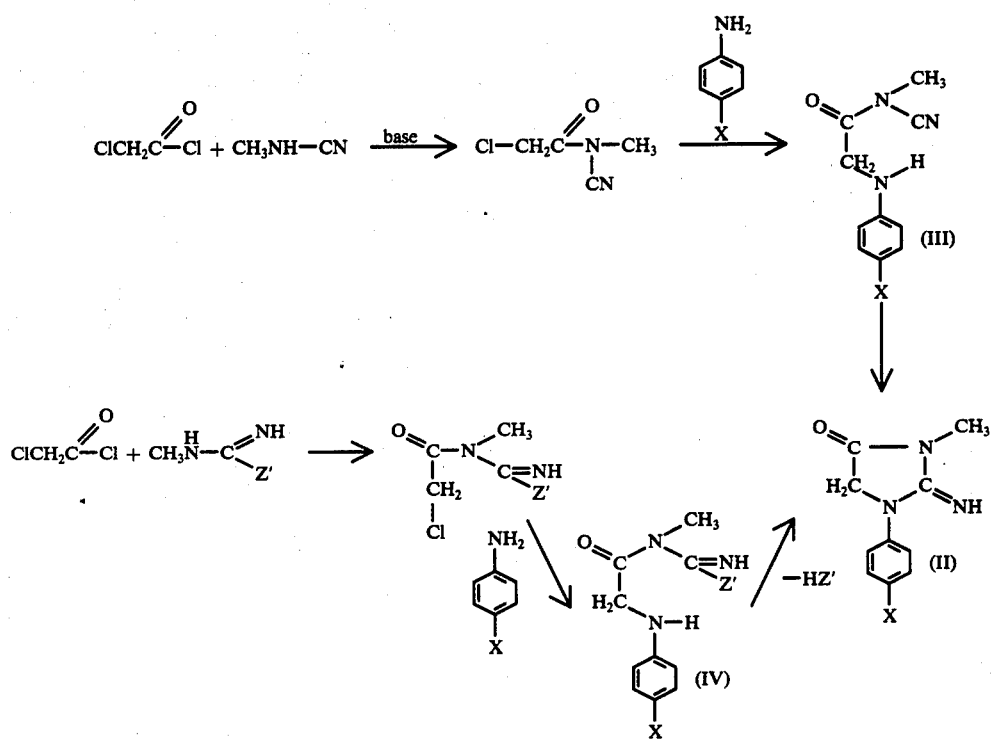
Z′ = NH, OCH$_3$, OH, SCH$_3$ or NHCH$_3$
The intermediates I and III can also be prepared from the N-(phenyl or p-chlorophenyl)glycine amides are their mono-anions and di-anions, respectively, as shown in the equations below.
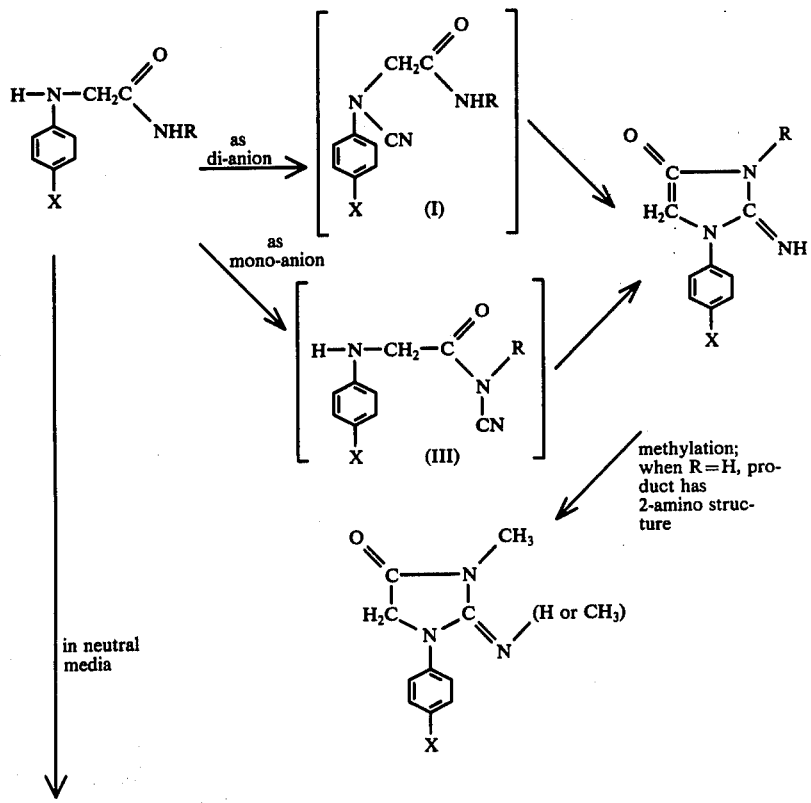

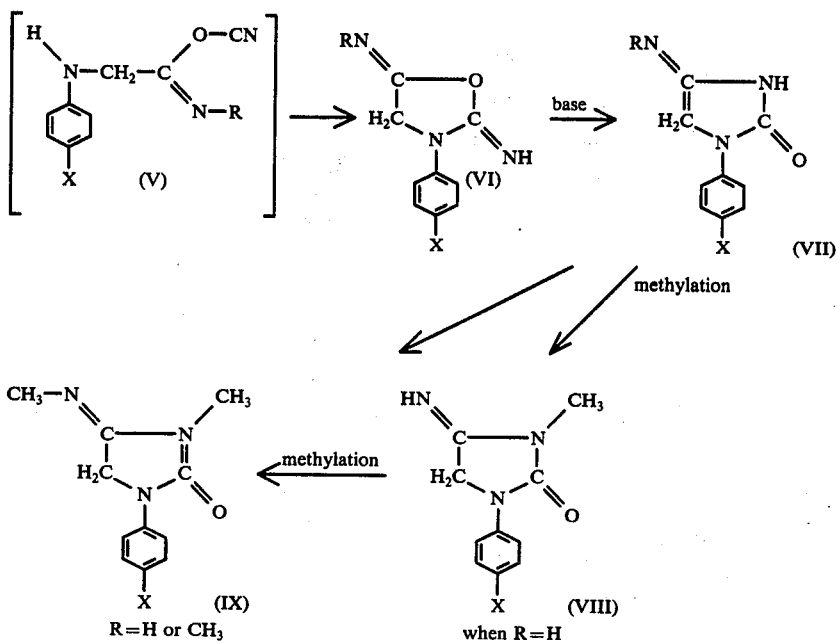

These N-(phenyl or p-chlorophenyl)glycine amides in neutral media serve as starting materials for the 4-imino-2-oxoimidazolidines VII, which are then mono- or dimethylated, as required, to give VIII and IX. This sequence proceeds through diiminooxazolidines VI as in the equations above; VI also gives a small or large amount of II depending on the conditions and the substituents present.

The 3-methyl compounds II are also synthesized by methylation of the imidazolidines X after cyclization. For this purpose, methyl sulfate, methyl methanesulfate, methyl toluenesulfonate, methyl fluorosulfonate, trimethyloxonium fluoroborate and other methylating agents are suitable. The cyclized material X is prepared as indicated.

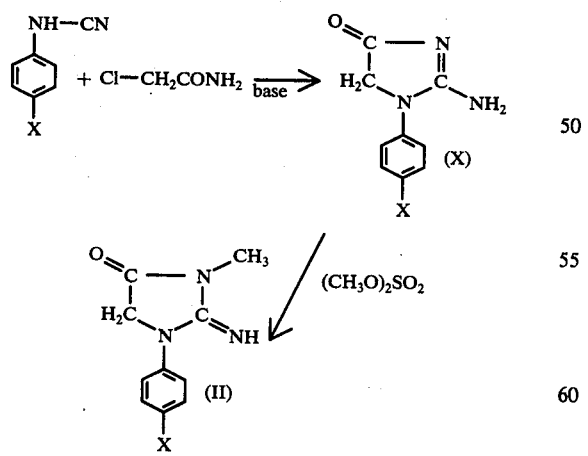

The dimethyl compounds below are prepared by carrying the N-methylation of the 3-methyl compound II further in situ or using the isolated 3-methyl compound prepared by the cyclization above of a α-substituted N-methyl acetamide.

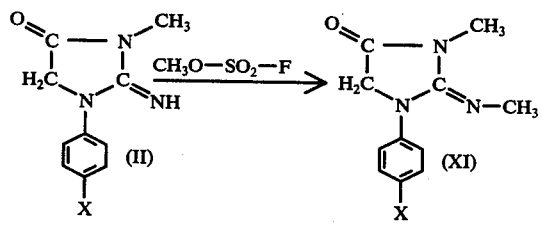

These dimethyl compounds XI are also obtained by isomerizing the 3-methyl compounds II with a catalyst such as alkoxide to 2-methylamino-2-imidazolines XII followed by methylation with a methylating agent as discussed above.

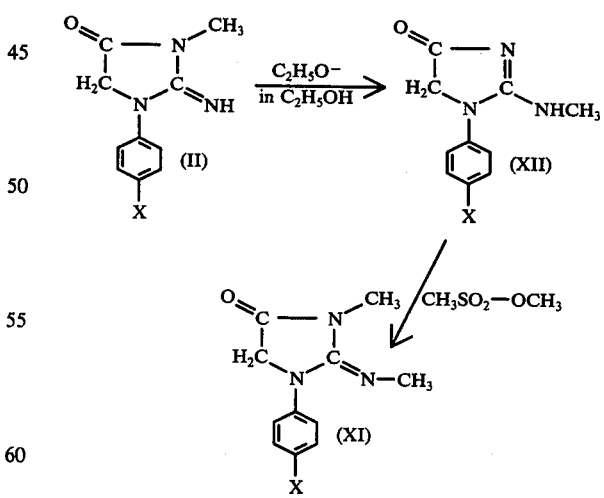

Another type of acyclic intermediate to the 2-imino-4-oxoimidazolidines II is the guanyl or isoureido structure XIII, analogous to structure IV. When XIII is a carboxylic acid, cyclization is usually accomplished in acidic solution, while when it is a lower alkyl ester, both acidic and basic media can be used.

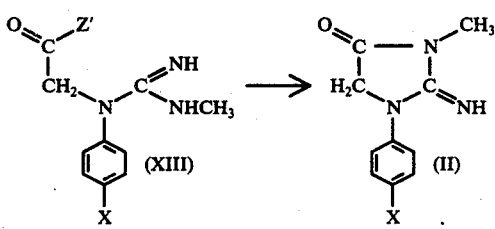

The 2,4-diimino compounds are prepared by the same reactions except that the carboxylic amide or ester group is replaced by a nitrile or an amidine group depending on the degree of methylation desired in the direct cyclization product.

Two standard test systems were used for the determination of antialdosterone diuretic activity for the tetrasubstituted imidazolidines. In the first model, compounds of this invention were initially tested in adrenalectomized, desoxycorticosterone-treated rats using the technique described by Kagawa [Proc. Soc. Exptl. Biol. Med. 99, 705 (1958).] Male Wistar rats weighing 150–200 g. were adrenalectomized under ether anesthesia. Following adrenalectomy, the animals were provided tap water and sugar tablets ad libitum until test time. Twenty-four hours postoperatively the animals were given 12.5 mcg. of desoxycorticosterone acetate subcutaneously in 0.1 ml. of corn oil. In addition, each animal received 2.5 ml. of 0.9% saline subcutaneously and the test compound suspended in 0.5 ml. of 2% starch suspension by gavage. Initially the test compounds were administered in a dose of 100 mg./kg. The rats were placed in metabolism cages, 2 animals per cage, and urine was collected for 4 hours. Urine volume was measured and urinary sodium and potassium were determined. In all experiments the steroidal anti-aldosterone drug, spironolactone, was run simultaneously as a standard for comparison. The results using 400 rats are shown in Table I. The percent change is shown as (+) greater or (−) less urinary excretion of ions from the control rats which received DCA (desoxycorticosterone acetate), but no drug.

TABLE I

Effect of Tetrasubstituted Imidazolidines on Electrolyte Excretion in Adrenalectomized, Desoxycorticosterone-treated Rats

| Compound | Dosage mg./kg. | Percent Change from Control Na+ | K+ |
|---|---|---|---|
| 1-(p-chlorophenyl)-2--imino-3-methyl-4-oxo-imidazolidine | 10 | 82 | −12 |
|  | 50 | 83 | −32 |
|  | 100 | 97 | −39 |
| 1-phenyl-2-imino-3--methyl-4-oxoimidazo-lidine | 1 | +9 | +4 |
|  | 5 | +45 | −22 |
|  | 10 | +76 | −4 |
|  | 25 | +129 | −3 |
|  | 50 | +132 | −9 |
|  | 100 | +290 | +33 |
| 1-phenyl-2-methylimino--3-methyl-4-oxoimidazo-lidine | 1 | +51 | +14 |
|  | 10 | +67 | +21 |
|  | 100 | +155 | −12 |
| 1-(p-chlorophenyl)-2--methylimino-3-methyl-4--oxoimidazolidine | 25 | +41 | −39 |
|  | 50 | +74 | −17 |
|  | 100 | +48 | −32 |
| 1-phenyl-4-imino-3--methyl-2-oxoimidazoli-dine | 10 | +51 | −6 |
|  | 50 | +32 | −41 |
|  | 100 | +127 | −19 |
| 1-phenyl-3-methyl-4-methylimino-2-oxoimida-zolidine | 25 | +36 | −66 |
| Spironolactone | 5 | +9 | −32 |
|  | 10 | +49 | −38 |
|  | 50 | +90 | −17 |
|  | 100 | +61 | −38 |

The second type of test was performed in conscious dogs utilizing a method described by Kagawa et al. (Kagawa, C. M., Bouska, D. J., Anderson, M. T. and Krol, W. F., Arch. Internat. Pharmacodyn. 149; 8–24, 1964). The left jugular vein was cannulated for infusion of solutions and a retention catheter was placed in the bladder for collection of urine. Some animals were given 0.25 mg. of DCS intramuscularly and the test drug orally by capsule 2 hours before the beginning of urine collections. Others received the test drug and corn oil rather than DCA. Saline 0.45% and dextrose 2.5% was infused intravenously throughout the experiment at a rate of 0.3 ml./kg./minute after a prime of 20 ml./kg. was given in approximately 20 minutes. Urine was collected at 30-minute intervals and blood samples were drawn from the right jugular vein at the midpoint of each collection period. Collections were continued for five 30-minute periods and the urinary Na and K effects in Table II are the average of the values for the five periods.

Table II records the results of the second type of test. Table II shows a favorable response also in dogs as indicated by substantial increase in sodium excretion without appreciable potassium loss.

TABLE II

The Effect of Tetrasubstituted Imidazolidines on Urinary Sodium and Potassium Excretion in Conscious Dogs in the Presence of Exogenous DCA

| Compound | Dosage mg./kg. | Percent Change from Control Na+ | K+ |
|---|---|---|---|
| 1-phenyl-2-imino-3--methyl-4-oxoimida-zolidine | 5 | 125 | 20 |
| 1-phenyl-2-imino-3--methyl-4-oxoimida-zolidine | 10 | 162 | 19 |
| 1-phenyl-2-imino-3--methyl-4-oxoimida-zolidine | 25 | 194 | 9 |
| 1-p-chlorophenyl-2--imino-3-methyl-4-oxoimidazolidine | 25 | 69 | 9 |

The tetrasubstituted imidazolidines of this invention serve as useful anti-aldosterone diuretics in doses of 1 mg. per kg. to 50 mg. per kg. of body weight per day. A preferred dosage regimen would be from 4 mg. per kg. to 20 mg. per kg. of body weight per day. When such dosage units are employed, a total daily intake of a subject of about 70 kg. body weight is about 70 mg. to 3.5 g., preferably about 280 mg. to 1.4 g.

The hydrochloride salts of 1-phenyl-2-imino-3-methyl-4-oxoimidazolidine and 1-p-chlorophenyl-2-imino-3-methyl-4-oxoimidazolidine are as active as the free bases when administered orally. They have the advantage that they are soluble enough to administer by injection, under which condition they are also highly active.

Tetrasubstituted imidazolidines according the present invention having the desired clarity, stability, and adaptability for parenteral use are obtained by dissolving the active compound in a vehicle consisting of a polyhydric aliphatic alcohol or mixtures thereof. Especially satisfactory are glycerin, propylene glycol, and the polyethylene glycols. The polyethylene glycols consist of a mixture of non-volatile, normally liquid, polyethylene glycols which are soluble in both water and organic liquids and which have molecular weights of from about 200 to about 1500. While concentrations can vary greatly, the amount of active compound dissolved in the above vehicle preferably should be from about 0.10 to about 10.0% by weight. Although various mixtures of the aforementioned non-volatile polyethylene glycols may be employed, it is preferred to use a mixture having an average molecular weight of from about 200 to about 400.

In addition to the active compounds, the parenteral solutions of the present invention may also contain various preservatives which may be used to prevent bacterial and fungal contamination. The preservatives which may be used for such purpose are, for example, benzyl alcohol, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, ascorbic acid, sodium bisulfite, sodium metabisulfite, and sodium formaldehyde sulfoxylate. Generally, from about 0.05 to about 0.2% concentrations of antioxidant are employed.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5 to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 100 and 500 milligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

In addition, the tetrasubstituted imidazolidines of this invention may advantageously be administered in a single combination with other diuretics such as those listed below, especially bumetanide, furosemide and hydrochlorothiazide. These diuretics may be incorporated with the tetrasubstituted imidazolidines and in the dosage below:

| Diuretic | Recommended daily human dosage range (mg./70 kg.) |
|---|---|
| hydrochlorothiazide | 100–200 |
| ethacrynic acid | 50–200 |
| furosemide | 40–80 |
| quinethazone | 50–100 |
| bumetanide | 1–2 |

In order to show the advantages of combining the compounds of this invention with known diuretic agents acting by other mechanisms, the following test was carried out. Rats were made sodium-deficient and hyperaldosteronic with low-sodium diet for a period of 2 weeks. The animals were deprived of food for approximately 18 hours prior to the test but had free access to water. At the beginning of the test, the animals wer given the test compound orally by gavage in aqueous starch suspension along with 10 ml. of 0.9% saline. Two rats were placed in each metabolism cage for urine collections. Urine samples were collected at 6 hours after dosing, their volume was measured, and their sodium, potassium and chloride ion concentrations were determined.

The effect of hydrochlorothiazide alone and in combination with two of the preferred tetrasubstituted imidazolidines of this invention is shown in Table III.

TABLE III

The Effect of Hydrochlorothiazide Alone and in Combination with Anti-aldosterone Diuretics in Sodium-Deficient Rats

| Treatment | Urine Volume (ml) | Na (mEq) | K (mEq) | Na/K ratio |
|---|---|---|---|---|
| Hydrochlorothiazide 5 mg/kg | 11.0 | 0.84 | 1.28 | 0.69 |
| Hydrochlorothiazide 5 mg/kg + Spironolactone 50 mg/kg | 12.2 | 1.41 | 1.20 | 1.53 |
| Hydrochlorothiazide 5 mg/kg + 1-phenyl-2-imino-3-methyl-4-oxo-imidazolidine 100 mg/kg | 17.4 | 1.71 | 1.45 | 1.18 |
| Hydrochlorothiazide 5 mg/kg + 1-(p-chlorophenyl-2-imino-3-methyl-4-oxo-imidazolidine 100 mg/kg | 15.7 | 1.63 | 1.33 | 1.26 |

The data in Table III shows that the combination of a thiazine diuretic (hydrochlorothiazide) with an aldosterone antagonist can lead to a greater sodium excretion without a significant increase in potassium excretion and hence a more favorable Na/K ratio. These data indicate that, with proper manipulation of dosage, sufficient sodium would be excreted without excessive potassium loss.

The use of combination therapy with a saluretic-diuretic and an aldosterone antagonist is indicated in certain instances. Secondary hyperaldosteronism as the result of a pathologic condition such as cirrhosis or as a result of vigorous diuretic therapy leading to hyponatremia is an underlying factor in refractoriness to diuretic agents and is an indication for the use of combination therapy. In addition, the use of an aldosterone antagonist in combination with another diuretic agent may allow the physician to reduce the dose of the primary diuretic and still get sufficient sodium excretion without excessive potassium loss.

Certain starting materials or intermediates used to prepare the tetrasubstituted imidazolidines of this invention can be prepared as follows:

PREPARATION OF INTERMEDIATES

I. 1-Phenyl-2-methylamino-4-oxo-2-imidazoline 2.2 g. of 1-phenyl-2-imino-3-methyl-4-oxoimidazolidine, 0.26 g. of sodium methoxide and 65 ml. of absolute alcohol were heated to reflux for 20 hours. The insoluble solid was filtered and ethanol was evaporated leaving a yellow solid.

The crude precipitate was chromatographed twice over silica gel and the product then recrystallized from acetone to yield 990 mg. (45%) of material, m.p. 208°–210° C. This product is used in Example 9.

II. 2,5-Diimino-3-phenyloxazolidine

To a mixture of 3.75 g. of antilinoacetamide, 2.5 g. of potassium bicarbonate and 50 ml. of ethanol was added rapidly 2.7 g. of cyanogen bromide in 20 ml. of ethanol. The reaction mixture was heated to reflux. After heating overnight and cooling, a small amount of precipitate was in the flask. This was filtered and the ethanolic filtrate shown to be slightly acidic. The ethanol filtrate was concentrated down to dryness leaving a solid which was washed with ethanol. The yield of product, m.p. 117°–9° C., was 3.9 g. (88%). The mass spectrum of the product gives a parent ion at m/e 175. This product is used to prepare intermediate III.

III. 1-Phenyl-4-amino-2-oxo-3-imidazoline

To 2.0 g. of 2,5-diimino-3-phenyloxazolidine dissolved in 50 ml. of absolute alcohol was added 0.6 g. of sodium methoxide. A white precipitate immediately formed in the solution. This was filtered, washed with ethanol, and dried to give 2.0 g. (100%) of product, m.p. 281°–283° C. The infrared spectrum matched the known 1-phenyl-4-amino-2-oxo-3-imidazoline. This product is used in Examples 10 and 11.

IV. 1-Phenyl-4-amino-2-oxo-3-imidazoline

To a mixture of 3.75 g. of antilinoacetamide, 2.5 g. of potassium bicarbonate and 40 ml. of ethanol was added dropwise 2.7 g. of cyanogen bromide in 20 ml. of ethanol. This mixture was heated to reflux overnight. On cooling, a light tan precipitate formed in the flask. The precipitate was filtered, washed with ethanol, water, and dried overnight. The yield of product, m.p. 277°–9° C. was 3.3 g. (75%). The mass spectrum of the compound gave a parent ion at m/e 175. An analytical sample was prepared by recrystallization from ethanol-methanol, m.p. 280°–2° C. In this case the ethanol filtrate was basic at the conclusion of the reaction leading to formation of the imidazoline in situ. This product is used in Examples 10 and 11.

V. 1-(p-Chlorophenyl)-2-methylamino-4-oxo-2-imidazoline

A mixture of 150 ml. of ethanol, 2.0 g. of 1-(p-chlorophenyl)-2-imino-3-methyl-4-oxoimidazolidine and 0.2 g. of sodium methoxide was heated to reflux for 20 hours. The solvent was removed on the rotating evaporator and the residue dissolved in acetone. The acetone solution was concentrated and the product obtained by crystallization from acetone-ether. The yield of product was 0.4 g. (20%), m.p. 204°–6° C. This product is used in Example 8.

The invention will now be described in greater detail in conjunction with the following specific examples of tetra-substituted imidazolidines within the scope of this invention.

EXAMPLE 1

1-p-Chlorophenyl)-2-imino-3-methyl-4-oxoimidazolidine

In 25 ml. of water containing 0.84 g. of sodium hydroxide was dissolved 3.2 g. of p-chlorophenylcyanamide. To the clear solution was added 2.25 g. of N-methylchloroacetamide. The reaction mixture was stirred for 48 hours at room temperature. The precipitate was filtered to yield 1.9 g. of product, m.p. 182°–184° C. After the initial product was filtered, the filtrate was left stirring another three days. An additional 1.2 g. of product precipitated from solution. Total yield of product was 3.1 g. (66%).

EXAMPLE 2

1-(p-Chlorophenyl)-2-imino-3-methyl-4-oxoimidazolidine 58 g. of p-chlorophenylcyanamide was dissolved in 600 ml. of absolute alcohol. To the solution was added 20.5 g. of sodium methoxide and the mixture was stirred for 30 minutes. Then 40.8 g. of N-methylchloroacetamide was added and the mixture was refluxed for 4 and ½ hours. The white solid was filtered, washed with ethanol and water. Its m.p. (183°–185° C.), infrared spectrum and thin-layer chromatography agreed with a previous sample. It weighed 63 grams (70.5% yield).

EXAMPLE 3

1-Phenyl-2-imino-3-methyl-4-oxoimidazolidine

In 29 ml. of water containing 1.0 g. of sodium hydroxide was dissolved 3.55 g. of phenylcyanamide. To the clear solution was added 2.7 g. of N-methylchloroacetamide. The reaction mixture was left to stir for 120 hours at room temperature. At that time no precipitate had formed. The solvent was therefore stripped off on a rotary evaporator under vacuum. The solid residue was slurried in dilute alkali and filtered to yield 1.0 g. (21%) of product, m.p. 163°–165° C.

EXAMPLE 4

1-Phenyl-2-imino-3-methyl-4-oxoimidazolidine 133 g. of phenylcyanamide hemihydrate was dissolved in 1500 ml. of absolute alcohol. To this solution was added 55 g. of sodium methoxide. This mixture was stirred for 30 minutes and 113 g. of N-methylchloroacetamide then added. This mixture was heated to reflux for 4 hours and allowed to stand overnight. The white precipitate was filtered and washed with ethanol. This ethanol filtrate was concentrated on the rotating evaporator and cooled giving additional product. Both crops of product were combined, washed with water and dried to give 87 g. (47%) of 1-phenyl-2-imino-3-methyl-4-oxoimidazolidine, m.p. 169°-170° C. The infrared spectrum and thin-layer chromatography of this product matched that of the previous sample.

EXAMPLE 5

1-Phenyl-2-imino-3-methyl-4-oxoimidazolidine

A mixture of 1.2 g. of 1-phenyl-2-amino-4-oxo-2-imidazoline, 15 ml. methylene chloride and 3.6 ml. of methylfluorosulfonate was left to stir at room temperature for 20 hours. The reaction was stopped and filtered to give 1.9 g. (94%) of the acid salt of the product. The isolation of the free base (m.p. 164°) is made by treating the salt with aqueous sodium hydroxide.

EXAMPLE 6

1-Phenyl-2-methylimino-3-methyl-4-oxoimidazolidine 3.78 g. of 1-phenyl-2-imino-3-methyl-4-oxoimidazolidine, 40 ml. dry methylene chloride and 6 ml. of methylfluorosulfonate are mixed and stirred in a flash equipped with a drying tube at room temperature. After 20 hours the solid was filtered and the filtrate was stripped to dryness. The residue was treated with 30 ml. of water and extracted once with ether. The aqueous layer was separated and added slowly to 12 ml. of 5N NaOH with cooling and stirring. The white precipitate was filtered, washed with water and dried. Thin-layer chromatography showed a single spot (Rf 0.6, 5% EtOH·CH$_2$Cl$_2$). The yield was 2.75 g. (68%), m.p. 116°-118° C.

EXAMPLE 7

1-(p-Chlorophenyl)-2-methylimino-3-methyl-4-oxoimidazolidine

By the method of Example 6 using 4.47 g. of 1-(p-chlorophenyl)-2-imino-3-methyl-4-oxoimidazolidine as starting material, 1-(p-chlorophenyl)-2-methylimino-3-methyl-4-oxoimidazolidine, m.p. 150°-152° C., was obtained.

EXAMPLE 8

1-(p-Chlorophenyl)-2-methylimino-3-methyl-4-oxoimidazolidine 3 g. of 1-(p-chlorophenyl)-2-methylamino-4-oxo-2-imidazoline and 9 ml. dimethyl sulfate were heated slowly to 120° C. with stirring. The reaction mixture, cooled to room temperature, was filtered. The clear filtrate diluted with 150 ml. H$_2$O was extracted once with 200 ml. ether. The aqueous layer was separated and made basic with 5N NaOH and cooling. The precipitate was filtered and recrystallized once with acetonitrile. Thin-layer chromatography gave a single spot. The yield of product, m.p. 150°-152° C., was 1.6 g. (50%).

EXAMPLE 9

1-Phenyl-2-methylimino-3-methyl-4-oxoimidazolidine

By the method of Example 8 using 2.5 g. of 1-phenyl-2-methylamino-4-oxo-2-imidazoline as starting material, 1-phenyl-2-methylimino-3-methyl-4-oxoimidazolidine, m.p. 116°-118° C., was obtained.

EXAMPLE 10

1-Phenyl-4-imino-3-methyl-2-oxoimidazolidine

To 0.4 g. of 1-phenyl-4-amino-2-oxo-3-imidazoline was added 1 ml. of dimethyl sulfate. This mixture was slowly heated to 160° C., over a 45-minute period. The reaction mixture was put onto the vacuum pump and warmed to 90° C. to remove excess dimethyl sulfate. To the reaction was added 10 ml. of absolute alcohol giving a white solid. This material, 400 mg., was filtered and dried. This solid material was then added to water where it rapidly dissolved giving an acidic solution. This indicates the desired compound had precipitated from ethanol as the methyl sulfuric acid salt. Addition of 5N sodium hydroxide precipitated the desired product; after filtering and drying, 260 mg. (61%) of 1-phenyl-4-imino-3-methyl-2-oxoimidazolidine was obtained. This material was then recrystallized from acetone to give pure product, m.p. 156°-158° C. The mass spectrum of the compound gave a parent peak at m/e 189.

EXAMPLE 11

1-Phenyl-3-methyl-4-methylimino-2-oxoimidazolidine

To 0.5 g. of 1-phenyl-4amino-2-oxo-3-imidazoline was added 1 ml. of dimethylsulfate. The reaction mixture was heated slowly to near reflux when all of the material went into solution. The solution was kept at this temperature for 10 minutes and allowed to cool. The reaction mixture was added to water and made basic with dilute sodium hydroxide. The reaction mixture was then stripped to a residue on the vacuum pump and the remaining material chromatographed. This gave the desired 1-phenyl-3-methyl-4-methylimino-2-oxoimidazolidine which was washed with hexane to give 85 mg. (15%), m.p. 160°-2° C. The mass spectrum of the compound gave a parent ion at m/e 203.

EXAMPLE 12

1-(p-Chlorophenyl)-2-imino-3-methyl-4-oxoimidazolidine hydrochloride 3.0 g. of 1-(p-chlorophenyl)-2-imino-3-methyl-4-oxoimidazolidine was dissolved in 25 ml. of ethanolic HCl. This solution was filtered and added to an excess of ether upon which the hydrochloride precipitated. This was filtered, dried, and recrystallized from ethanol to give 0.8 g. product, m.p. 276°-8° C. the ethanol filtrate was concentrated to give an additional 1.1 g. of material. The total yield of product was 1.9 g. (55%).

EXAMPLE 13

1-Phenyl-2-imino-3-methyl-4-oxoimidazolidine hydrochloride 1.0 g. of 1-phenyl-2-imino-3-methyl-4-oxoimidazolidine was dissolved in 20 ml. of hot ethanol. This solution was added to 25 ml. of ethanolic HCl. No precipitate formed. This solution was then added to an excess of ether and the product precipitated. This was filtered and dried to give 1.0 g. (85%) of product, m.p. 279°-281° C.

EXAMPLE 14

The present compounds can be dispensed in dosage unit forms such as soft shell or hard shell capsules. A formulation useful in the preparation of such capsules is as follows:

| Ingredients | Grams per 100 capsules |
| --- | --- |
| 1-phenyl-2-imino-3-methyl--4-oxoimidazolidine | 45 |
| lactose, U.S.P. | 300 |
| magnesium stearate (0.5%) | 3.1 |
| Total | 348.1 |

The above formulation is thoroughly mixed and placed in equal quantities in 100 capsules.

EXAMPLE 15

The following example represents a formulation useful in preparing tablets. Larger tablets can be scored and divided in halves to be given once or twice a day. Smaller tables can be used in multiple doses to obtain the daily amount of active material. The following formulation has been found useful:

| Ingredients | mg. per tablet |
| --- | --- |
| 1-(p-chlorophenyl)-2-imino--3-methyl-4-oxoimidazolidine | 450 |
| corn starch | 210 |
| methyl cellulose 400 | 350 |
| magnesium stearate; 1% | 182 |
| Total | 1192 |

The active ingredient, corn starch and methyl cellulose are blended together. The mixture, after drying, is lubricated with 1% magnesium stearate and compressed into tablets in a suitable tableting machine.

EXAMPLE 16

The following example represents a formulation useful in preparing an oral syrup:

| | |
| --- | --- |
| 1-phenyl-2-imino-3-methyl-4-oxo-imidazolidine | 4500 mg. |
| sorbitol solution (70% N.F.) | 40 ml. |
| sodium benzoate | 150 mg. |
| saccharin | 10 mg. |
| red dye (F.D. and C. No. 2) | 10 mg. |
| cherry flavor | 50 mg. |
| distilled water, q.s. ad | 100 ml. |

The sorbitol solution is added to 40 ml. of distilled water and the active ingredient is suspended therein. The saccharin, sodium benzoate, flavor and dye are added and dissolved in the above solution. The volume is adjusted to 100 ml. with distilled water. Each ml. of syrup contains 45 mg. of drug.

EXAMPLE 17

For the preparation of a parental solution the following procedure is followed. In a solution of 700 ml. of propylene glycol and 200 of water for injection is dissolved 20.0 g. of 1-(p-chlorophenyl)-2-imino-3-methyl-4-oxoimidazolidine with stirring. After dissolution is complete, a solution of 2.5 g. of ascorbic acid in 20 ml. of water is then added. The pH of this solution is adjusted to 5.5 with hydrochloric acid and the volume is made up to 1.0 liter with distilled water. The formulation is filtered through a 0.22 micron sterilizing filter, filled into 5.0 ml. ampules each containing 2.0 ml. (representing 40 mg. of drug) and sealed under nitrogen.

We claim:
1. 1-(p-chlorophenyl)-2-imino-3-methyl-4-oxoimidazolidine.
2. 1-phenyl-2-methylimino-3-methyl-4-oxoimidazolidine.
3. 1-(p-chlorophenyl)-2-methylimino-3-methyl-4-oxoimidazolidine.
4. 1-phenyl-4-imino-3-methyl-2-oxoimidazolidine.
5. 1-phenyl-4-methylimino-3-methyl-2-oxoimidazolidine.
6. 1-(p-chlorophenyl)-2-imino-3-methyl-4-oxoimidazolidine hydrochloride.

* * * * *